(12) United States Patent
Miwa et al.

(10) Patent No.: US 8,728,794 B2
(45) Date of Patent: May 20, 2014

(54) STRAIN CONFERRING ANTI-DISEASE PROPERTIES TO HOST AND BACTERIAL CELL COMPOSITION

(75) Inventors: Takehiro Miwa, Yokohama (JP); Hiroshi Watanabe, Yokohama (JP); Mamoru Ishihara, Yokohama (JP); Tsuneo Hino, Sagamihara (JP); Narito Asanuma, Kawasaki (JP)

(73) Assignee: Meiji Seika Pharma Co., Ltd., Tokyo (JP)

( * ) Notice: Subject to any disclaimer, the term of this patent is extended or adjusted under 35 U.S.C. 154(b) by 1485 days.

(21) Appl. No.: 11/813,021

(22) PCT Filed: Dec. 28, 2005

(86) PCT No.: PCT/JP2005/024144
§ 371 (c)(1),
(2), (4) Date: Jun. 28, 2007

(87) PCT Pub. No.: WO2006/070891
PCT Pub. Date: Jul. 6, 2006

(65) Prior Publication Data
US 2008/0095745 A1 Apr. 24, 2008

(30) Foreign Application Priority Data
Dec. 28, 2004 (JP) ................................. 2004-379693

(51) Int. Cl.
*C12N 1/20* (2006.01)
(52) U.S. Cl.
USPC ....................................... 435/252.1; 424/93.4
(58) Field of Classification Search
None
See application file for complete search history.

(56) References Cited

U.S. PATENT DOCUMENTS

2002/0082436 A1  6/2002  Jerome et al.

FOREIGN PATENT DOCUMENTS

| JP | 2001-503430 A | 3/2001 |
|----|---------------|--------|
| JP | 2003-73269 A | 3/2003 |
| WO | 02/080947 A1 | 10/2002 |
| WO | 03/043972 A2 | 5/2003 |
| WO | 03/087344 A1 | 10/2003 |
| WO | 2004/031395 A1 | 4/2004 |

OTHER PUBLICATIONS

Kim et al., Applied and Environmental Microbiology, Dec. 2000, p. 5226-5230 vol. 66, No. 12.*
Kepler et al., 1966 The Journal of Biological Chemistry, 241, pp. 1350-1354.*
Ha et al.. Applied and Environmental Microbiology, 1991, p. 2016-2020, vol. 57, No. 7.*
Kalmoff et al.. Applied and Environmental Microbiology, Feb. 1997, p. 394-402 vol. 63, No. 2.*
Masatsugu Fukuda et al., "Kyoyaku Linoleic acid Seisanno no Takai Shoka Kannai Saikin, Butyrivibrio fibrisolves no Kyoyaku Linoleic acid Kangen Koso no Seisei", Annual Meeting of the Molecular Biology Scienty of Japan Program Koen Yoshishu, Nov. 25, 2004, p. 858.
Extended European Search Report dated Oct. 7, 2008.
Ohkawara et al., "Oral Administration of *Butyrivibrio fibrisolvens*, a Butyrate-Producing Bacterium, Decreases the formation of Aberrant Crypt Foci in the Colon and Rectum of Mice", Journal of Nutrition, vol. 135, No. 12, Dec. 2005, pp. 2878-2883 (XP002496292).
Asanuma, Narito et al., "Presence of Butyrivibrio fibrisolvens in the digestive tract of dogs and cats, and its contribution to butyrate production" *J. Gen. Appl. Microbiol.*, vol. 47, p. 313-319, 2001.
Office Action dated Mar. 17, 2011, in Korean Application No. 10-2007-7016857.
Japanese Patent Office, Office Action issued Jul. 8, 2011 in corresponding Japanese Patent Application No. 2006-550863.

\* cited by examiner

*Primary Examiner* — Irene Marx
(74) *Attorney, Agent, or Firm* — Sughrue Mion, PLLC

(57) ABSTRACT

The present invention provides a novel bacterial cell composition which comprises cells of *Butyrivibrio fibrisolvens* having the ability to produce butyric acid, a cultured material thereof or an extract thereof, and a method for inhibiting carcinogenesis, a method for immunostimulating, a method for preventing or treating a pathogen, a method for preventing or treating an inflammatory bowel disease and a method for preventing or treating an allergic disease, which use the same.

6 Claims, 2 Drawing Sheets

D: Administration of DMH

B: Administration bacterial cells

M: Measurement

● : No administration of 3-MC and bacterial cell composition

■ : Administration of 3-MC and non-administration of bacterial cell composition

▲ : Administration of 3-MC and bacterial cell composition

STRAIN CONFERRING ANTI-DISEASE PROPERTIES TO HOST AND BACTERIAL CELL COMPOSITION

TECHNICAL FIELD

The present invention relates to a novel bacterial cell composition which comprises cells of *Butyrivibrio fibrisolvens* (to be referred also to as *B. fibrisolvens* hereinafter) having high butyric acid producing ability and is useful in inhibiting carcinogenesis, improving immunity, preventing and treating pathogenic infection, preventing and treating inflammatory bowel disease and preventing and treating allergic diseases.

BACKGROUND OF THE INVENTION

In recent years, probiotics preparations using *Lactobacillus, Bifidobacterium* and the like having high lactic acid producing ability have been reported (Patent Reference 1) and many of them have been on the market. Basic function of the preparations is regulating the functions of the intestine. When a host ingests the preparations, pH in the intestinal tract is lowered due to the lactic acid produced by a lactic acid producing strain included in the preparations. Accordingly, it is considered that the number of unfavorable bacteria which cannot grow under such a low pH environment is reduced, and the regulation of intestinal functions is shown as a result thereof. The general idea as the probiotics which brings effects such as health improvement and disease resistance to the hosts by such a microbial function is broadly accepted socially, and the effects have been also recognized. The probiotics according to the present invention means a viable microorganism which show useful activities upon the health of animals and humans.

Further recently, it has been reported not only on the lactic acid produced by the lactic acid bacteria, but also on the fact that the lactic acid bacteria has the immunostimulating activity to host by peptidoglycan and the like proteins which are contained in the provided microbial cells themselves and bacteriocin which shows a narrow range of antibacterial activity for certain specific bacteria (Non-patent reference 1).

Additionally, short-chain fatty acids produced by the enteric fermentation in humans and animals have been drawn attention. With regard to the short-chain fatty acids, their function which lowers pH in the intestinal tract, effects which accelerate movement of intestine (Non-patent reference 2), and accelerate absorption of Na and the like have been shown. Among the short-chain fatty acids, butyric acid is particularly drawing attention. As its functions, it has been shown that it is important as an energy source of colon epithelial cells (Non-patent reference 3) and that it brings very useful effects for hosts, such as its anticancer activity (Non-patent reference 4) and its effect to accelerate differentiation of intestinal mucosa cells.

However, there is a problem in view of its characteristic odor and safety when butyric acid is directly and orally administered. Thus, it seems to be effective to produce it in the intestine in a small amount and to carry out its continuous absorption in host, rather than its direct oral administration, in order to allow such an important physiological active substance to act on a host more effectively.

As an accelerator of entericbutyric acid concentration which uses a microorganism, those which use cells of *Lactobacillus acidophilus* and/or *Bifidobacterium longum* as an active ingredient have been disclosed (Patent Reference 2). However, there is no description in the document on their effect regarding actual diseases, and the degree of disease resistance due to administration of the cells is unclear.

Also, a method has been disclosed, which uses *Clostridium butyricum* (to be referred also to as *C. butyricum* hereinafter) as the microorganism having ability of producing butyric acid (Non-patent Reference 5). According to such an already known reference, the *Clostridium butyricum* which is already put on the market as a butyric acid producing bacterium has the regulation of the functions of intestines. However, regarding its effect for inhibiting precancerous lesion cells, there is a problem that effect by the microorganism alone is low, since it is necessary to administer it together with a special substrate in order to obtain sufficient effect (Non-patent Reference 6). Also, as a result of the investigation of preventive effect on inflammatory bowel disease carried out in the same manner, there is a problem that the effect by the microorganism alone is low.

Additionally, these references do not clearly describe an illustrative method which uses *Butyrivibrio fibrisolvens* as a probiotics, and its effects are not revealed therein, too.

Based on the above, great concern has been directed toward a bacterial strain which has a high disease resistant activity due to having further high health improving, anticancer and immunostimulating functions for a host and also has the ability to produce butyric acid, Patent Reference 1: JP-A-2002-306125
Patent Reference 2: JP-A-10-84909
Non-patent Reference 1: Kawai Y et al., *Curr. Protein. Pept. Sci.*, 2004, 5(5), 393-8, "The circular bacteriocins gassericin A and circulacin A"
Non-patent Reference 2: Cherbut, C. et al., *American Journal of Physiology*, 1998, 275, G1415-G1422, "Short-chain fatty acids modify colonic motility through nerves and polypeptide YY release in the rat"
Non-patent Reference 3: Cummings, J. H., *Gut*, 1981, 22, 763-779, "Short-chain fatty acids in the human colon"
Non-patent Reference 4 Hague, A. et al., *Gastroenterology*, 1997, 112, 1036-1040, "Butyrate acts as a survival factor for colonic epithelial cells: further fuel for the in vivo versus in vitro debate"
Non-patent Reference 5: Kanauchi O. et al., *Curr. Pharm. Des.*, 2003, 9(4), 333-346, "Modification of intestinal flora in the treatment of inflammatory bowel disease"
Non-patent Reference 6: Nakanishi S. et al., *Microbiol. Immunol.*, 2003, 47(12), 951-958, "Effects of high amylose maize starch and *Clostridium butyricum* on metabolism in colonic microbiota and formation of azoxymethane-induced aberrant crypt foci in the rat colon".

DISCLOSURE OF THE INVENTION

Problems Solved by the Invention

An object of the present invention is to provide bacterial cells of a newly isolated *Butyrivibrio fibrisolvens* having carcinogenesis inhibitory effect, immunostimulating effect, pathogen infection preventing and treating effect, inflammatory bowel disease preventing and treating effect and allergic disease preventing and treating effect. Also, since the bacterial strain has high butyric acid producing ability and can be used as a probiotics, its further object is to provide a method for inhibiting carcinogenesis, a method for immunostimulation, a method for preventing and treating pathogen, a method for preventing and treating inflammatory bowel disease and a method for preventing and treating allergic disease.

Means for Solving the Problems

The inventors of the present invention have conducted intensive studies seeking for a probiotics preparation having further health improving, anticancer and immunostimulating functions for humans and animals and also having the ability to produce butyric acid in the intestine, which is safe and can be provided inexpensively. They have found that *Butyrivibrio fibrisolvens* have such functions and accomplished the present invention.

That is, the present invention is shown in the following.

(1) A *Butyrivibrio fibrisolvens* MDT-1 strain deposited as FERM BP-10463 in International Patent Organism Depositary, National Institute of Advanced Industrial Science and Technology, and a mutant strain thereof.

The *Butyrivibrio fibrisolvens* MDT-1 strain and a mutant strain thereof are preferable as probiotics and have high butyric acid producing ability.

(2) A bacterial cell composition which comprises bacterial cells of at least one species of a microorganism belonging to the genus *Butyrivibrio*, a cultured material or extract thereof.

(3) The bacterial cell composition according to (2) wherein the microorganism which belongs to the genus *Butyrivibrio* is *Butyrivibrio fibrisolvens*.

(4) The bacterial cell composition according to (3), wherein the *Butyrivibrio fibrisolvens* is a strain which belongs to *Butyrivibrio fibrisolvens* type I (which is a type having high butyric acid producing ability).

(5) The bacterial cell composition according to (3), wherein the *Butyrivibrio fibrisolvens* is *Butyrivibrio fibrisolvens* MDT-1 strain deposited as FERM BP-10463 in International Patent Organism Depositary, National Institute of Advanced Industrial Science and Technology, and a mutant strain thereof.

(6) A pharmaceutical preparation which comprises the bacterial cell composition described in any one of (2) to (5) as an active ingredient.

(7) A feed additive which comprises the bacterial cell composition described in any one of (2) to (5) as an active ingredient.

(8) A therapeutic agent for inhibiting cancer development, which comprises the bacterial cell composition described in any one of (2) to (5) as an active ingredient.

(9) A method for inhibiting carcinogenesis, which comprises administering an effective amount of the bacterial cell composition described in any one of (2) to (5) to human or a vertebral animal.

(10) An immunostimulating agent which comprises the bacterial cell composition described in any one of (2) to (5) as the active ingredient.

(11) A method for immunostimulating, which comprises administering an effective amount of the bacterial cell composition described in any one of (2) to (5) to human or a vertebral animal.

(12) An agent for preventing and/or treating infection with a pathogen, which comprises the bacterial cell composition described in any one of (2) to (5) as an active ingredient.

(13) A method for preventing and/or treating infection with a pathogen, which comprises administering an effective amount of the bacterial cell composition described in any one of (2) to (5) to human or a vertebral animal.

(14) An agent for preventing and/or treating an inflammatory bowel disease, which comprises the bacterial cell composition described in any one of (2) to (5) as an active ingredient.

(15) A method for preventing and/or treating an inflammatory bowel disease, which comprises administering an effective amount of the bacterial cell composition described in any one of (2) to (5) to human or a vertebral animal.

(16) An agent for preventing and/or treating an allergic disease, which comprises the bacterial cell composition described in any one of (2) to (5) as the active ingredient.

(17) A method for preventing and/or treating an allergic disease, which comprises administering an effective amount of the bacterial cell composition described in any one of (2) to (5) to human or a vertebral animal.

Effect of the Invention

The bacterial cell composition of the present invention has anticancer activity, immunostimulating effect, preventing and treating effect of inflammatory bowel disease, preventing and treating effect of pathogen infection and preventing and treating effect of allergic disease and the like.

BEST MODE FOR CARRYING OUT THE INVENTION

Figure 1:
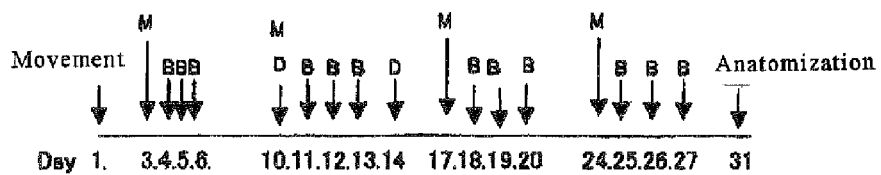
FIG. 1 is a drawing which shows administration schedule of bacterial cell composition and dimethylhydrazine.

The following describes the present invention in detail.

The "type I" of *Butyrivibrio fibrisolvens* according to the specification is a kind of the classification of the bacterium based on the difference in the fermentation ability (Shane B S et al. *J. Gen. Microbiol.*, 1969, 55, 445-457, "Cellulolytic bacteria occurring in the rumen of sheep contained to low-protein teff hay"). The type I forms a large amount of butyric acid, since its fermentation pathway is inclined toward butyric acid production, and the ratio of lactic acid formed by bacterial fermentation is small in comparison with type IIb.

As shown in the tables the MDT-1 strain of the present invention has the most high resistance to lowering of extracellular pH among the type I strains which produces large amount of butyric acid. Therefore, it is expected that this grows advantageously even in the acidic intestinal tract.

TABLE 1

Minimum growth pH of *B. fibrisolvens*

| Strain | Type | Minimum growth pH |
|---|---|---|
| TH-1 | IIb | 5.2 |
| MDT-1 | I | 5.3 |
| 51255 | IIb | 5.5 |
| A38 | I | 5.8 |
| OB156 | IIb | 6.0 |

The term "method for inhibiting carcunogenesis" as used herein means for example, a method for preventing formation of aberrant crypt foci which is a precancerous lesion of large intestinal tract mucous membrane. Namely, in a case of ordinary state wherein there is completely no possibility of carcinogenesis or in a case wherein there is a possibility of carcinogenesis, the carcinogenesis can be completely prevented or its risk can be reduced, by administering the bacterial cells or bacterial cell composition of the present invention or a pharmaceutical preparation containing the same to a human or animal in advance. Also in the same manner, when there is a possibility that carcinogenesis was already occurred, the cancer development can be prevented or reduced, by immediately administering the bacterial cells or bacterial cell composition of the present invention or a pharmaceutical preparation containing the same to a human or animal.

The term "method for immunostimulation" as used herein means for example, a method for further reinforcing immunity when a pathogenic bacterium, virus or the like entered the body of a human or animal, by increasing the number of NK cells for quickly showing disease resistance, quickness or efficacy of the response of humoral immunity such as IgG production, or quickness or efficacy of the response of the intestinal tract immune system. Namely, in a case of ordinary state wherein there is completely no possibility of causing infection with a pathogenic bacterium or virus or in a case wherein there is a possibility of infection with a pathogenic bacterium or virus, infection with the aforementioned pathogenic bacterium or virus entered into the body can be completely prevented or reduced, by administering the bacterial cells or bacterial cell composition of the present invention or a pharmaceutical preparation containing the same to a human or animal in advance. Also in the same manner, when there is a possibility that a pathogenic bacterium or virus was already entered the body, onset or crisis of diseases caused by the aforementioned infection with a pathogenic bacterium, virus or the like can be prevented or reduced, by immediately administering the bacterial cells or bacterial cell composition of the present invention or a pharmaceutical preparation containing the same to a human or animal.

Also, the term "method for preventing and/or treating infection with a pathogenic bacteria" as used herein means for example a method for preventing infection with the pathogenic bacterium, or onset and crisis of diseases caused by the infection when a pathogenic bacterium which is represented by the genus *Salmonella* or the genus *Campylobacter* enters the digestive tract or respiratory tract of a human or animal. Namely, in a case of ordinary state wherein there is completely no possibility of infection or in a case where there is a possibility of infection, the aforementioned infection with a pathogenic bacterium can be completely prevented or reduced, by administering the bacterial cells or bacterial cell composition of the present invention or a pharmaceutical preparation containing the same to a human or animal in advance. Also in the same manner, when there is a possibility that a subject is already infected with a pathogenic bacterium, onset and crisis of diseases caused by the aforementioned infection with a pathogenic bacterium can be completely prevented or reduced, by immediately administering the bacterial cells or bacterial cell composition of the present invention or a pharmaceutical preparation containing the same to a human or animal.

The term "method for preventing and/or treating inflammatory bowel disease" as used herein means a method for preventing and/or treating, for example, development of a symptom or disease of an intractable disease known as ulcerative colitis or Crohn disease. That is, the aforementioned disease can be completely treated or its symptoms can be alleviated, by administering the bacterial cells or bacterial cell composition of the invention or a pharmaceutical preparation containing the same to a human or animal already suffered from the aforementioned disease. Also in the same manner, in the case of ordinary state with completely no possibility of suffering from the aforementioned disease or having a possibility of suffering from the aforementioned disease, the aforementioned disease can be prevented or alleviated, by administering the bacterial cells or bacterial cell composition of the invention or a pharmaceutical preparation containing the same to a human or animal in advance.

The term "method for preventing and/or treating allergic disease" as used herein means for example an effect for improving and/or treating symptoms of an allergic disease by inclining Th1/Th2 balance of helper T cells which are immune cells to Th1. Specifically, the allergic disease shows atopic dermatitis, pollinosis, diarrhea caused by a food-originated component, and the like symptoms. Namely, in the case of ordinary state wherein there is completely no possibility of showing allergic symptoms or in case there is a possibility of crisis of allergic symptoms, crisis of the allergic symptoms can be completely prevented or its risk can be reduced, by administering the bacterial cells or bacterial cell composition of the present invention or a pharmaceutical preparation containing the same to a human or animal in advance. Also in the same manner, when there is a possibility that an allergic symptom was already shown, progress of the allergic symptom can be prevented or alleviated, by immediately administering the bacterial cells or bacterial cell composition of the present invention or a pharmaceutical preparation containing the same to a human or animal.

Origin of the bacterial cell in the bacterial cell composition of the present invention is not particularly limited, as long as that it shows various characteristics described above. As the origin, it is preferably a microorganism which belongs to the genus *Butyrivibrio*, more preferably *Butyrivibrio fibrisolvens*, further preferably a strain classified into type I of *Butyrivibrio fibrisolvens*, particularly preferably *Butyrivibrio fibrisolvens* MDT-1 (FERM BP-10463). With regard to mutant strains of MDT-1, they are not limited as long as that the effects of the present invention can be obtained therefrom. An example of that includes a sub-cultured strain, an artificial mutant strain and a natural mutant strain, a recombinant strain and the like of MDT-1. Bacteriological properties of the MDT-1 strain are as follows.

Bacteriological Properties of MDT-1

*Butyrivibrio fibrisolvens* strain MDT-1 is a Gram-negative bacillus. The bacterium is a strictly anaerobic bacterium which requires high anaerobic degree for its growth. Sugar utilization of the bacterium is shown in the following table.

TABLE 2

Sugar utilization of *B. fibrisolvens* MTD-1[1]

| bacteria | Sugars[2] | | | | | | | | | |
|---|---|---|---|---|---|---|---|---|---|---|
| | Glu | Mal | Fru | Gal | Lac | Ara | Xyl | Cel | Sta | Avi |
| Isolated bacterium | ++ | + | ++ | ++ | + | + | ++ | ++ | ++ | − |
| *B. fibrisolvens* | ++ | + | ++ | ++ | + | + | ++ | ++ | ++ | − |

[1]Regarding the sugar utilization, remaining amounts after 24 hours of culturing were measured and divided based on the consumed amounts: "++" indicates 20 mM or more of consumption; "+" indicates 5 mM or more of consumption; and "−" indicates less than 5 mM of consumption.
[2]Glu = glucose, Man = mannose, Fru = fructose, Gal = galactose, Lac = lactose, Ara = arabinose, Xyl = xylose, Cel = cellobiose, Sta = corn starch, Avi = avicel (microcrystalline cellulose).

Additionally, the fermentation products which are formed at the time of the growth of the bacterium are as follows.

TABLE 3

Fermentation products at the time of the growth of *B. fibrisolvens* MTD-1[1)]

| Bacteria | Fermentation products[2)] | | | | |
|---|---|---|---|---|---|
| | Lactic acid | Formic acid | Acetic acid | Butyric acid | Total amount |
| Isolated bacterium | 11.8 | 9.9 | 10.3 | 11.3 | 43.3 |
| *B. fibrisolvens* | 12.2 | 9.7 | 9.8 | 11.5 | 43.2 |

[1)]Fermentation products after 24 hours of culturing using glucose and cellobiose (2 g/l for each) as the substrates.
[2)]Succinic acid and propionic acid were not detected in both bacteria.

In this connection, the *Butyrivibrio fibrisolvens* MDT-1 strain was deposited on Nov. 9, 2004, as FERM P-20293 in International Patent Organism Depositary, National Institute of Advanced Industrial Science and Technology (address: Central 6, 1-1 Higashi 1-chrome, Tsukuba, Ibaraki, Japan) (in this connection, the MDT-1 strain was transferred to the International Depositary on Dec. 5, 2005 as FERM BP-10463).

Culturing method of the MDT-1 strain is described in the following.

When *Butyrivibrio fibrisolvens* is cultured in the present invention, a general nutrient medium can be used as long as that it contains a component which shows buffering ability at around neutral pH, and both of a natural medium and synthetic medium can be used as long as that they sufficiently contain a carbon source, a nitrogen source, metals, short-chain fatty acids, vitamins and amino acids.

With regard to the carbon source in the medium, glucose, fructose, sucrose, maltose, mannose, starch and the like can be used. Also, peptone, yeast, meat extract and the like can be used as the nitrogen source. Additionally, as the inorganic salts, dipotassium hydrogenphosphate, potassium dihydrogenphosphate, sodium chloride potassium chloride, ammonium sulfate, magnesium sulfate, potassium acetate and the like can be used.

With regard to the culturing method, *Butyrivibrio fibrisolvens* can be cultured by agitation-culturing at from 10° C. to 70° C., preferably from 25° C. to 60° C., more preferably from 30 to 45° C., for from 2 to 96 hours, preferably from 3 to 48 hours, more preferably from 5 to 24 hours, with keeping more high anaerobic degree through replacement of the atmosphere with carbon dioxide gas, nitrogen gas or the like.

The bacterial cell composition of the present invention contains bacterial cells of the aforementioned microorganism which belongs to the genus *Butyrivibrio*, a cultured material thereof or an extract thereof. An example of the cultures material includes culture supernatant and the like obtained by culturing the bacterium in the aforementioned manner. An example of an extract includes an extract obtained by extracting effective components from a lysate prepared by carrying out lysis of the bacterial cells. It is preferable that the bacterial cell composition of the present invention contains cells of the aforementioned microorganism which belongs to the genus *Butyrivibrio*, since the effects of the present invention can be expressed more effectively.

The following describes the bacterial cell composition of the present invention with reference to a case in which the bacterial cell composition of the present invention contains cells of the aforementioned microorganism which belongs to the genus *Butyrivibrio*.

A precipitate containing the bacterial cells is obtained by treating the obtained culture liquid. Additionally, the bacterial cell composition can also be obtained by suspending the bacterial cells in an isotonic solution or the like solution. As the isotonic solution or the like solution, a sodium chloride solution or the like can be used.

In order to obtain the bacterial cell composition of the present invention which comprises a microorganism having the ability to produce butyric acid, the bacterial cell composition of the present invention can be prepared by carrying out culturing under conditions which is appropriate for the microorganism as described above, followed by recovering cells comprising the microorganism of the present invention, and if necessary, adding optional components (a solution, cells other than said cells, a carrier, a diluent and the like).

The content of bacterial cells in the bacterial cell composition is not particularly limited as long as sufficient functions as described in above can be shown according to the application purpose. For example, the content can be from 0.01 to 99% by mass, preferably from 0.1 to 80% by mass, based on the total weight of the bacterial cell composition.

In addition to the bacterial cells of the invention, the bacterial cell composition of the present invention can further contain bacterial cells other than the bacterial cells of the invention, such as those of at least one of the genus *Lactobacillus*, the genus *Bifidobacterium* and the genus *Clostridium*. When bacterial cells other than the bacterial cells of the present invention are used in combination, further improvement of the effect as a probiotics can be expected in comparison with the bacterial cell composition containing the bacterial cells of the present invention alone.

The bacterial cell composition of the present invention can contain the bacterial cells of the present invention alone as the active ingredient, or can contain an appropriate carrier and/or diluent together with the bacterial cells of the present invention as the active ingredient. As the aforementioned carrier and/or diluent, a carrier or a diluent generally used as the carrier or diluent of bacterial cell compositions, such as an excipient (e.g., lactose, sodium chloride, sorbitol or the like), a surfactant or an antiseptic, can be used as long as that the carcinogenesis inhibitory effect, immunostimulating effect, preventing and treating effect of pathogen infection, preventing and treating effect of inflammatory bowel disease and preventing and treating effect of allergic disease the bacterial cells of the present invention as the active ingredient are not suppressed or inhibited thereby.

By using of the bacterial cells or bacterial cell composition of the present invention alone or in the form of the aforementioned pharmaceutical preparations, inhibition of carcinogenesis, improvement of immunity, prevention of pathogenic infection, prevention of inflammatory bowel disease and prevention of allergic disease in a human or a host animal can be effected. Alternatively, even when a human or a host animal already has a cancer; reduced its immunity; has a possibility of infection with a pathogen; has a possibility of infection by a inflammatory bowel disease; or has a possibility of infection by an allergic disease, each symptom can be treated or alleviated by administering the bacterial cells or bacterial cell composition of the present invention.

The objective organism according to the present invention is not particularly limited, as long as that it is an organism in which the effects of the present invention can be effectively expressed. Its examples include human or animals. An example of the animals includes vertebral animals such as pet animals and domestic animals can be exemplified, and particularly, fishes, amphibians, reptiles, birds, mammals and the like. Their illustrative examples includes fishes, amphibians and reptiles which is cultivated or treasured, birds which are treasured, pet animals such as dogs, cats and rodents, domestic animals such as cattle and pigs and domestic fowls.

With regard to the administration of the bacterial cells or bacterial cell composition of the present invention, an embodiment by which the bacterial cells or bacterial cell composition can reach the digestive tract is desirable, and an embodiment by which it can reach the intestine is further desirable. An example of embodiment includes oral administration by tablets, pills, capsules, granules, fine granules, powders, oral solutions for oral use or the like, and parenteral administration which uses suppositories.

Amount of the aforementioned bacterial cell composition to be contained as the active ingredient in the medicines, feed additives, carcinogenesis inhibitors, immunostimulators, agents for preventing and treating pathogenic infection, agents for preventing and treating inflammatory bowel disease and agents for preventing and treating allergic diseases of the present invention is not particularly limited as long as that the effects of the invention can be obtained, and when it is expressed by the amount of bacterial cells, it is preferably from $10^3$ to $10^{14}$ cfu/g, more preferably from $10^5$ to $10^{13}$ cfu/g, and particularly preferably from $10^6$ to $10^{12}$ cfu/g.

Administration method of the aforementioned bacterial cell composition which is the active ingredient (dose, administration frequency, administration period) in the medicines, feed additives, carcinogenesis inhibitors, immunostimulators, agents for preventing and treating pathogenic infection, agents for preventing and treating inflammatory bowel disease and agents for preventing and treating allergic disease of the invention and the methods of the present invention is not particularly limited as long as that the aforementioned bacterial cells can reach the intestines and can grow in the intestines, and the effects of the present invention can be obtained. Thus, it can be appropriately set by taking the objective animal, purpose and growing state of the bacterial cells into consideration.

The dose is not particularly limited as long as that the effects of the present invention can be obtained, but when it is expressed by the amount of bacterial cells per one administration, it is preferably from $10^3$ to $10^{15}$ cfu, more preferably from $10^6$ to $10^{14}$ cfu, and particularly preferably from $10^8$ to $10^{12}$ cfu, per 1 kg of objective animal.

The dose of the aforementioned range may be, for example, administered once or continuously administered over a certain period of time. In the case of the continuous administration, the administration period is, for example, preferably from 2 days to 6 months or more, more preferably from 3 days to 6 months or more, particularly preferably from 7 days to 6 months or more. According to the present invention, the effects of the present invention can be further expressed by continuing the administration over further prolonged period of time.

In the case of the continuous administration, the administration frequency is, for example, preferably once or more of administration in 1 month, more preferably once or more of administration in 2 weeks, particularly preferably from once a week to everyday of administration.

With regard to the administration method, by setting the daily dose to the aforementioned range, the whole dose may be administered once a day, or may be administered by dividing it into 2 to 3 times a day. Alternatively, it may be administered by mixing with feed or the like in such a manner that the daily dose belongs to the aforementioned range.

EXAMPLES

Although the present invention is illustratively described in the following based on Examples, these do not limit the scope of the present invention, and all of their changing or modifying means which are not shown herein are included herein.

Example 1

Preparation of Bacterial Cell Composition

In order to obtain the bacterial cell composition of the invention, a medium consisting of 0.9 g of dipotassium hydrogenphosphate (mfd. by Wako Pure Chemical Industries), 0.9 g of potassium dihydrogenphosphate (mfd. by Wako Pure Chemical Industries), 1.8 g of sodium chloride (mfd. by Wako Pure Chemical Industries), 1.8 g of ammonium sulfate (mfd. by Wako Pure Chemical Industries), 0.24 g of calcium chloride dehydrate (mfd. by Wako Pure Chemical Industries), 0.375 g of magnesium sulfate heptahydrate (mfd. by Wako Pure Chemical Industries), 1 g of potassium acetate (mfd. by Wako Pure Chemical Industries), 0.5 g of sodium propionate (mfd. by Wako Pure Chemical Industries), 0.3 g of sodium n-butyrate (mfd. by Wako Pure Chemical Industries), 0.1 g of valeric acid (mfd. by Wako Pure Chemical Industries), 0.1 g of isobutyric acid (mfd. by Wako Pure Chemical Industries), 0.1 g of isovaleric acid (mfd. by Wako Pure Chemical Industries), 0.1 g of 2-methyl butyrate (mfd. by Wako Pure Chemical Industries), 10 mg of ammonium iron citrate (mfd. by Wako Pure Chemical Industries), 6 mg of manganese chloride (mfd. by Wake Pure Chemical Industries), 2 mg of cobalt sulfate (mfd. by Wako Pure Chemical Industries), 0.4 mg of nickel chloride (mfd. by Wako Pure Chemical Industries), 0.4 mg of ammonium molybdate (mfd. by Wake Pure Chemical Industries), 1 mg of 15% cupper sulfate (mfd. by Wako Pure Chemical Industries), 0.3 mg of aluminum potassium sulfate (mfd. by Wako Pure Chemical Industries), 0.3 mg of boric acid (mfd. by Wako Pure Chemical Industries), 2 mg of zinc sulfate (mfd. by Wako Pure Chemical Industries), 2 mg of pyridoxal phosphate (mfd. by Wako Pure Chemical Industries), 0.5 mg of p-aminobenzoic acid (mfd. by Wake Pure Chemical Industries), 0.2 mg of biotin (mfd. by Wako Pure Chemical Industries), 2 mg of phenyl propionate (mfd. by Kanto Chemical Co., Ltd.), 2 mg of L-arginine (mfd. by Wake Pure Chemical Industries), 100 mg of Panvitan (mfd, by Takeda Chemical Industries), 0.03 μl of Vitamin $K_1$ (mfd. by SIGMA), 3 g of glucose (mfd. by Wako Pure Chemical Industries), 3 g of Yeast Extract (mfd by Difco), 1.5 g of Tryptone Peptone (mfd, by Becton Dickinson and Company), 1.5 g of Typticase (mfd. by Becton Dickinson and Company) and 1 g of cysteine hydrochloride (mfd. by Wako Pure Chemical Industries) (pH 7.0) (to be referred to as medium A hereinafter) was subjected to $CO_2$ replacement and sealed in a container and heat-sterilized. Then *Butyrivibrio fibrisolvens* MDT-1 (FERM BP-10463) was inoculated into the medium A (40 ml) and cultured at 37° C. for 5 hours with stirring. By centrifuging the thus obtained culture medium using a centrifuge (3000 G, 30 minutes), a precipitate containing the bacterial cells was obtained. Next, a bacterial cell composition was obtained by suspending the bacterial cells in 0.8% NaCl solution to a bacterial cell density of $10^{10}$ cfu/ml.

Example 2

Inhibitory Effect on ACF Formation

Using the bacterial cell composition of the present invention, evaluation of its ability to inhibit formation of aberrant crypt foci (ACF) induced by mouse DMH (dimethylhydrazine; mfd. by Aldrich) was carried out. Additionally, the same test was carried out also on *Clostridium butyricum* already on the market as a butyric acid bacterium, and their inhibitory effects were compared.

Male Jcl:ICR mice of 4 weeks of age (CLEA Japan, Inc.) were used as the animal to be tested. The test was carried out by setting the test plots as shown in the following table, with 10 animals per plot.

The bacterial cell composition obtained by the method described in Example 1 was orally administered to the mice by force using a gastric tube. To the control group, 0.1 ml ($10^9$ cfu) portion of 0.8% NaCl solution was administered, and the same portion of the bacterial cell composition to the administration group. Administration schedule of the bacterial cell composition and dimethylhydrazine (DMH; mfd. by Aldrich) is as shown in FIG. 1.

Aberrant crypt foci (ACF) as a precancerous lesion of large intestinal tract mucosa were measured on the 31st day after start of the test. After subjecting each mouse to euthanasia, a part of the mouse intestinal tract, which is from under the blind gut to the anus, was extracted and fixed with 10% formalin (mfd. by Junsei Chemical) after cutting open the central part. After that, it was stained with methylene Blue (mfd. by Kanto Chemical, Co., Ltd.), and the ACF were counted using an optical microscope.

TABLE 4

Test Section

| Groups | The number of animals | Administration of DMH | Administration of bacterial cells |
|---|---|---|---|
| No administration of DMH and bacterial cells | 10 | 0.8% NaCl | 0.8% NaCl |
| Administration of DMH and non-administration of bacterial cells | 10 | DMH 50 mg/kg body weight | 0.8% NaCl |
| Administration of DMH and *B. fibrisolvens* | 10 | DMH 50 mg/kg body weight | $10^9$ cfu 3 times/week |
| Administration of DMH and *C. butyricum* | 10 | DMH 50 mg/kg body weight | $10^9$ cfu 3 times/week |

Although body weight gain was reduced by the administration of DMH, it was improved by the oral administration of the bacterial cell composition of the present invention (Table 5). Such an effect was not found by the oral administration of *C. butyricum*. Significant difference was not found in the mass of the liver at the time of completion of the test (Table 6). The liver mass per body weight was reduced by the administration of DMH and improved to similar level of the DMH non-administration group by administrating the bacterial cell composition of the present invention. Mass of the spleen was increased by the administration of DMH, and improved to a certain degree by the bacterial cell composition of the present invention. Such effects were not found by *C. butyricum*.

TABLE 5

Changes in body weight

| | Mouse body weight (g) | | | | |
|---|---|---|---|---|---|
| Groups | 3 days | 10 days | 17 days | 24 days | 31 days |
| No administration of DMH and bacterial cells | 27.8 ± 0.2 | 28.9 ± 0.3 | 35.9 ± 0.5 | 38.4 ± 0.5 | 40.5 ± 0.7[a] |
| Administration of DMH and non-administration of bacterial cells | 27.8 ± 0.3 | 27.7 ± 0.5 | 32.8 ± 0.9 | 35.4 ± 0.7 | 34.6 ± 1.0[b] |
| Administration of DMH and *B. fibrisolvens* | 27.7 ± 0.4 | 30.1 ± 0.7 | 33.2 ± 0.7 | 36.1 ± 0.8 | 37.9 ± 0.7[c] |
| Administration of DMH and *C. butyricum* | 27.8 ± 0.2 | 28.8 ± 0.2 | 31.5 ± 1.0 | 35.4 ± 0.6 | 34.9 ± 0.7[b] |

[a-c]It is shown that there is a significant difference between opposite signs. ($p < 0.05$)

TABLE 6

Organ weight

| | Organ weight (g) | |
|---|---|---|
| groups | Liver (body weight ratio %) | Spleen (body weight ratio %) |
| No administration of DMH and bacterial cells | 2.23 ± 0.10 (5.5 ± 0.3)[a] | 0.105 ± 0.004 (0.260 ± 0.007)[a] |
| Administration of DMH and non-administration of bacterial cells | 2.48 ± 0.09 (7.2 ± 0.2)[b] | 0.496 ± 0.014 (1.441 ± 0.053)[b] |
| Administration of DMH and *B. fibrisolvens* | 2.26 ± 0.08 (5.8 ± 0.1)[a] | 0.301 ± 0.030 (0.771 ± 0.069)[c] |
| Administration of DMH and *C. butyricum* | 2.47 ± 0.11 (7.1 ± 0.4)[b] | 0.514 ± 0.024 (1.481 ± 0.086)[b] |

[a-c]It is shown that there is a significant difference between opposite signs. ($p < 0.05$)

Conditions of Intestinal Tract and ACF

The length from the colon to the rectum was shortened by the administration of DMH and improved to a certain degree by the bacterial cell composition of the present invention. Also, mass of the blind gut and mass of the colon and rectum were reduced by the administration of DMH and improved to a certain degree by the bacterial cell composition of the present invention. No difference was found regarding the pH of contents of the blind gut and contents of the colon. Additionally, the number of formed ACF was controlled to about half by orally administering the bacterial cell composition of the present invention. Such effects were not found also by *C. butyricum*.

TABLE 7

Length of colon rectum, weight of blind gut and colon rectum and pH of contents of blind gut and colon rectum

| Groups | Length (cm) of colon rectum | Organ weight (g) Blind gut | Organ weight (g) colon rectum | pH Blind gut contents | pH colon rectum contents |
|---|---|---|---|---|---|
| No administration of DMH and bacterial cells | 10.9 ± 0.3[a] | 0.207 ± 0.012[a] | 0.426 ± 0.017[a] | 6.5 ± 0.0 | 6.7 ± 0.0 |
| Administration of DMH and non-administration of bacterial cells | 8.4 ± 0.2[b] | 0.111 ± 0.012[b] | 0.264 ± 0.015[b] | 6.5 ± 0.0 | 6.7 ± 0.0 |
| Administration of DMH and *B. fibrisolvens* | 9.3 ± 0.4[c] | 0.163 ± 0.018[c] | 0.338 ± 0.024[c] | 6.5 ± 0.0 | 6.7 ± 0.0 |
| Administration of DMH and *C. butyricum* | 8.5 ± 0.3[b] | 0.115 ± 0.007[b] | 0.258 ± 0.012[b] | 6.5 ± 0.0 | 6.7 ± 0.0 |

[a-c]It is shown that there is a significant difference between opposite signs. ($p < 0.05$)

TABLE 8

The number of formed ACF

| Groups | The number of formed ACF |
|---|---|
| No administration of DMH and bacterial cells | 0 ± 0.0[a] |
| Administration of DMH and non-administration of bacterial cells | 14.7 ± 1.2[b] |
| Administration of DMH and *B. fibrisolvens* | 7.4 ± 0.8[c] |
| Administration of DMH and *C. butyricum* | 15.7 ± 1.2[b] |

[a-c]It is shown that there is a difference between opposite signs. ($p < 0.05$)

Example 3

Immune Acceleration Effect

Degree of acceleration of immunity in a host was examined by measuring NK cell which is considered to firstly attack foreign substances entered into a body such as a pathogen and a virus.

Male Jcl:ICR mice of 8 weeks of age (CLEA Japan, Inc.) were used as the animal to be tested, and the test was carried out by 3 animals per group.

The bacterial cell composition obtained by the method described in Example 1 was orally administered to the mice by force using a gastric tube. After administrating 0.1 ml ($10^9$ cfu) portion of 0.8% NaCl solution to the control group, and the same portion of the bacterial cell composition to the administration plot. The administration was carried out continuously for 3 days, and each mouse was sacrificed 1 week after the first administration.

The spleen was extracted from the mouse sacrifice by cervical vertebrae dislocation, and spleen cells were prepared therefrom. After carrying out lysis erythrocytes, the cells were washed twice and suspended in PBBS (a buffer; see table) to a density of $10^7$ cells/ml. To 100 μl of the thus prepared spleen lymphocyte suspension, 10 μl portion of each of the antibodies which are described in the following was added and allowed to stand on ice for 30 minutes. Thereafter, it was washed twice with PBBS and used in the measurement. FACSCalibur (Becton, Dickinson and Company) was used for the measurement of the cells. An FITC-labeled anti-CD3 antibody (mfd. by Beckman Coulter, Inc.), a PE-labeled anti-CD19 antibody (mfd. by Beckman, Coulter, Inc.) and a PE-labeled anti-NK1.1 antibody (mfd. by Beckman Coulter, Inc.) were used in the labeling of the cells.

By oral administration of the bacterial cell composition, ratios of T cell and B cell in the lymphocytes were reduced, and ratios of NK cell and NKT (natural killer T) cell were increased (Table 10). When it is converted to the number of cells, influence of the oral administration of the bacterial cell composition upon the number of T cells and B cells was not found (Table 11). However, the number of NK cells was increased to be 3.5 times, and the number of NKT cells was increases to be 3.8 times. Accordingly, oral administration of the bacterial cell composition to mice accelerates their immune function.

TABLE 9

PBBS (phosphate-buffered balanced salt solution) (0.1% BSA added)

| | |
|---|---|
| NaCl | 7.20 g |
| KCl | 0.32 g |
| $Na_2HPO_4$ | 1.15 g |
| $KH_2PO_4$ | 0.20 g |
| $CaCl_2$ | 0.14 g |
| $MgCl_2 \cdot 6H_2O$ | 0.20 g |
| $MgSO_4 \cdot 7H_2O$ | 0.20 g |
| Glucose | 1.00 g |
| BSA | 1.00 g |
| $H_2O$ | Up to 1 L |

All manufactured by Kanto Chemical, except for BSA (mfd. by Wako Pure Chemical Industries).

TABLE 10

Existence ratio of lymphocytes

| Groups | T cell (%) | B cell (%) | NK cell (%) | NKT cell (%) | Others (%) |
|---|---|---|---|---|---|
| Control group | 17.2 | 53.4 | 4.6 | 0.8 | 24.1 |
| Test group | 16.5 | 42.3 | 14.4 | 2.5 | 24.4 |

TABLE 11

| | The number of lymphocytes | | | | |
|---|---|---|---|---|---|
| Groups | T cell | B cell | NK cell | NKT cell | Others |
| Control Group | $8.9 \times 10^6$ | $2.8 \times 10^7$ | $2.4 \times 10^6$ | $3.9 \times 10^5$ | $8.0 \times 10^7$ |
| Administration Group | $9.5 \times 10^6$ | $2.5 \times 10^7$ | $8.4 \times 10^6$ | $1.5 \times 10^6$ | $7.1 \times 10^7$ |

Example 4

Pathogen Infection Preventive Effect

*Campylobacter* is a causative bacterium of food poisoning, which is orally taken from feces or polluted food and settled in the intestinal tract. Accordingly, whether or not the *Butyrivibrio fibrisolvens* MDT-1 strain has the effect to prevent infection was examined.

Male Jcl:ICR mice of 5 weeks of age (CLEA Japan, Inc.) were used as the animal to be tested, and the test was carried out by 10 animals per plot.

The bacterial cell composition obtained by the method described in Example 1 was orally administered to the mice by force using a gastric tube. To the control group, 0.2 ml ($10^9$ CFU/ml) portion of 0.8% NaCl solution was administered and the same portion of the bacterial cell composition was administered to the administration group. The administration was carried out continuously for 3 days which was started from 4 days before the infection. Two days thereafter, a *Campylobacter coli* strain 11580-3 (domestic fowl origin) was orally inoculated in 0.2 ml ($10^7$ CFU/ml) portions. The bacterial cell composition was administered continuously for 4 days, which was started on the next day of the infection in the same manner as the before the infection. Each animal was sacrificed on the 5th day after the infection and anatomized to collect blind gut feces. It was diluted with 0.8% NaCl by a 10-fold serial dilution system and applied to a *Campylobacter* 10% sheep blood agar medium (Japan Becton Dickinson and Company). After 48 hours of culturing at 42° C. in an anaerobic incubator, the number of viable cells (colonies) was counted to calculate the number of *Campylobacter* cells per 1 g blind gut feces (log CFU/g).

Mortal cases were not observed in both control plot and bacterial cell composition group.

As shown in Table 12, the number of *Campylobacter* cells in the blind gut feces was 8.27 log CFU/g in average (from 7.88 to 8.82 log CFU/g) in the control plot and 6.96 log CFU/g in average (from 4.79 to 8.69 log CFU/g) in the bacterial cell composition group. In comparison with the control plot, the bacterial cell composition group showed a significant reduction of 1.31 log CFU/g.

Based on the above results, infection with *Campylobacter* was reduced when the bacterial cell composition was administered. That is, it was revealed that prevention or reduction of infection can be effected by continuing taking of the bacterial cell composition.

TABLE 12

Infection preventive effect on *Campylobacter*
The number of *C. coli* cells in blind gut (log CFU/g)

| | Average ± S.D. |
|---|---|
| Control Group | 8.27 ± 0.30 |
| Bacterial Cell Composition Group | 6.96 ± 1.47* |

*There is a significant difference: P < 0.05

Example 5

Inflammatory Bowel Disease Preventive Effect

Inflammatory bowel disease (IBD) such as ulcerative colitis and Crohn disease is an intractable disease. Accordingly, whether or not the *Butyrivibrio fibrisolvens* MDT-1 strain also has a similar effect was examined.

Male Jcl:ICR mice of 4 weeks of age (CLEA Japan, Inc.) were used as the animal to be tested, and the test was carried out by 6 animals per group.

The bacterial cell composition obtained by the method described in Example 1 was orally administered to the mice by force using a gastric tube. To the control plot, 0.1 ml ($10^9$ CFU) portion of 0.8% NaCl solution was administered and the same portion of the bacterial cell composition was administered to the administration group. The administration was carried out continuously for 3 days.

In order to induce IBD, dextran sulfate sodium (DSS; mfd. by MP Biomedical) was dissolved in drinking water to a concentration of 3% (w/v) and allowed to be freely taken by the mice. Administration of DSS was carried out for 7 days, which was started on the next day of the 3 days of continuous administration of the bacterial cell composition. On the $8^{th}$ day, each mouse was sacrificed and anatomized to measure length and mass of the intestinal tract.

Calculation of disease activity index (DAI) was carried out in the following manner. Namely, each of the reduction of body weight, shape of feces (degree of diarrhea) and occult blood was evaluated by 5 steps of from 0 to 4. In this case, serious symptoms were evaluated by higher values. A value calculated by divining total numbers of these three measuring items by 3 was used as the DAI.

Measuring method of myeloperoxidase (MPO) was carried out in the following manner. That is, a 6 cm in length of a terminal part of the large intestine was suspended in a 20 mmol/l phosphate buffer (pH=6.0) containing 5 ml/l (v/v) of hexadecyltrimethylammonium bromide (HTAB; a surfactant) (mfd. by Wako Pure Chemical Industries) and subjected to ultrasonic disintegration. After centrifugation (15,000 rpm, 15 min), 0.1 ml portion of the supernatant was mixed with 2.9 mL of a 20 mM phosphate buffer (pH=6.0) containing 20 mM guaiacol (mfd. by SIGMA) and 5 ml/l hydrogen peroxide (mfd. by Kanto Chemical Co., Ltd.), and change in the absorbance at a wavelength of 460 nm was measured and used as the MPO activity.

As shown in Table 6, the body weight was reduced by the DSS administration, but the degree of reduction was reduced in the mice which were orally administered with the bacterial cell composition,

TABLE 13

Changes in mice body weight by DSS and *B. fibrisolvens* administrations

| DSS admin. | B. fibrisolvens admin. | Before admin. | Mice body weight (g) (n = 6) DSS administered days | | | | | | |
|---|---|---|---|---|---|---|---|---|---|
| | | | 1 | 2 | 3 | 4 | 5 | 6 | 7 |
| − | − | 28.1$^a$ | 29.4$^a$ | 29.7$^a$ | 30.0$^a$ | 31.3$^a$ | 31.8$^a$ | 32.5$^a$ | 33.7$^a$ |
| + | − | 28.1$^a$ | 29.0$^a$ | 29.3$^a$ | 29.5$^a$ | 29.7$^b$ | 29.5$^c$ | 28.2$^c$ | 26.5$^c$ |
| + | + | 28.0$^a$ | 29.0$^a$ | 29.4$^a$ | 29.8$^a$ | 29.9$^b$ | 30.2$^b$ | 29.9$^b$ | 30.2$^b$ |

$^{a-c}$Opposite sign shows the presence of significant difference (P < 0.05, n = 6).

Although increase of the spleen, reduction of the liver and shortening of the large intestine were observed by the administration of DSS, but the degree of these changes was reduced by the administration of the bacterial cell composition (Table 14).

TABLE 14

Weights of the spleen and the liver and length of the intestinal tract of mice which was administered DSS or *B. fibrisolvens*

| DSS administration | B. fibrisolvens administration | Organ weight (g) | | Intestinal tract length (colon-rectum) (cm) |
|---|---|---|---|---|
| | | Spleen | Liver | |
| − | − | 0.11$^a$ | 2.35$^a$ | 11.2$^a$ |
| + | − | 0.24$^c$ | 1.56$^c$ | 7.2$^c$ |
| + | + | 0.17$^b$ | 1.99$^b$ | 8.9$^b$ |

$^{a-c}$Opposite sign shows the presence of significant difference (P < 0.05, n = 6).

Figure 2:
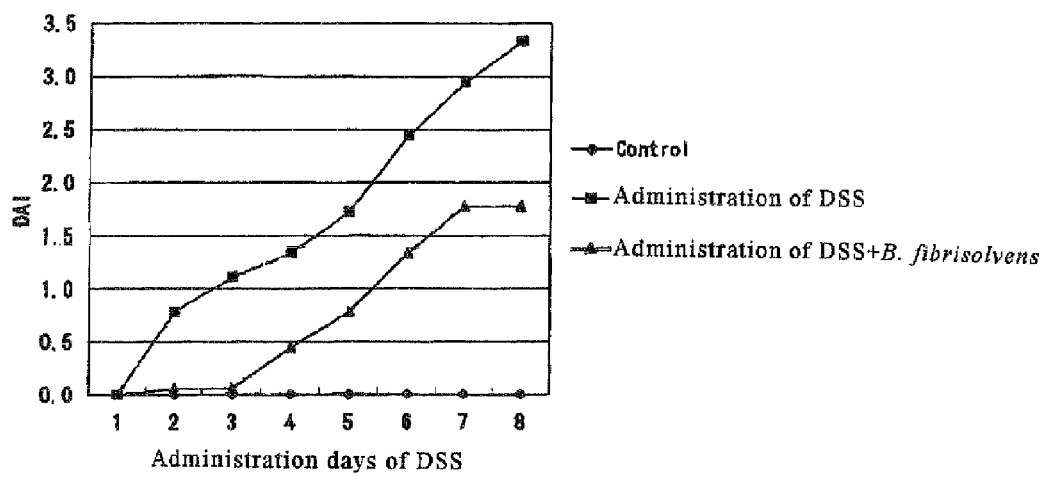
FIG. 2 is a drawing which shows DAI in DSS- and *Butyrivibrio fibrisolvens*-administered mice.

Also from the DAI values obtained by converting each of the reduction of body weight, shape of feces and occult blood into numerical values, it was considered that the disease conditions were alleviated by the administration of the bacterial cell composition (FIG. 2). Additionally, the MPO activity of the intestinal tract tissue in the mice which was administered the bacterial cell composition was reduced to about 40% of that of the mice which was administered DSS alone (Table 15). Based on this result, it is considered that the degree of inflammation was low due to less neutrophil in the intestinal tract of the mice to which the bacterial cell composition was administered.

TABLE 15

MPO activity in intestinal tract of mice which was administered DSS or *B. fibrisolvens*

| DSS administration | B. fibrisolvens administration | MPO relative activity |
|---|---|---|
| − | − | 20$^c$ |
| + | − | 100$^a$ |
| + | + | 43$^b$ |

$^{a-c}$Opposite sign shows the presence of significant difference (P < 0.05, n = 6).

Based on the above result, oral administration of the bacterial cell composition alleviated the symptoms. Namely, it was revealed that the inflammatory bowel disease can be prevented when the bacterial cell composition is continuously taken.

Example 6

Antiallergic Activity

The number of NK (natural killer) cells in the spleen was increased by the oral administration of *Butyrivibrio fibrisolvens* to mice. The NK cell forms a cytokine IFN-γ. IFN-γ has the ability to incline the Th1/Th2 balance of helper T cell to Th1. The Th1/Th2 balance is an index which effects on allergy. Accordingly, whether or not *Butyrivibrio fibrisolvens* is effective also on an allergic disease was examined by measuring cytokine.

*Butyrivibrio fibrisolvens* MAT-1 strain was cultured in 20 ml of a synthetic medium until it reached metaphase of the logarithmic growth phase. The bacterial cells were washed once with PBS (a buffer liquid) and recovered by centrifugal precipitation, followed by suspension in RPMI-1640 medium (mfd. by KOHJIN BIO) containing 10% bovine serum (JRH Bioscience), in such a manner that the number of bacterial cells became $4 \times 10^7$ cells/ml.

The spleen was extracted from a mouse, and spleen cells were prepared therefrom. After carrying out lysis of erythrocytes, the cells were washed twice and suspended in RPMI-1640 medium (mfd. by KOHJIN BIO) containing 10% bovine serum (JRH Bioscience), to a density of $4 \times 10^7$ cells/ml. To a culture dish, 0.5 ml portion of the spleen cell suspension was added and 0.5 ml of the bacterial liquid or medium was further added thereto, followed by incubation for 72 hours in a 5% $CO_2$ incubator.

Determination of cytokine was carried out in the following manner. Namely, the cell culture liquid was subjected to centrifugal precipitation and the resulting supernatant was used as the sample. Determination of quantity of IFN-γ and IL-4 was carried out using an ELISA kit (Amersham Biosciences) and in accordance with the instructions attached thereto.

As a result, production of IFN-γ was increased by the addition of *Butyrivibrio fibrisolvens* MDT-1 strain. On the other hand, production of IL-4 which has the ability to incline the Th1/Th2 balance to Th2 was lowered (Table 16). It is considered that the Th1/Th2 balance inclines toward the Th1 side by the presence of *Butyrivibrio fibrisolvens* MDT-1 strain. Accordingly, oral administration of *Butyrivibrio fibrisolvens* MDT-1 strain is also effective for allergic diseases.

TABLE 16

Relative amounts of cytokines IFN-γ and IL-4 in mouse spleen cells

| B. fibrisolvens (cfu) | Relative amounts (%) | |
|---|---|---|
| | IFN-γ | IL-4 |
| 0 | 100 | 100 |
| $1 \times 10^7$ | 596 | 15 |

Example 7

Influence Upon Sarcoma Formation

In order to confirm whether or not there is an inhibitory effect on a cancer formed in a region other than the large intestine, influence on fibrosarcoma formation in mice induced by subcutaneous administration of 3-methylcholanthrene (3-MC) was examined.

The test was carried out on three groups of a 3-MC non-administration/bacterial cell composition non-administration group (10 animals), a 3-MC administration/bacterial cell composition non-administration group (13 animals) and a 3-MC administration/bacterial cell composition administration plot (11 animals). To each of the Jcl:ICR mice of 4 weeks of age (CLEA Japan, Inc.), 0.1 ml ($10^9$ CFU) portion of the bacterial cell composition obtained by the method described in Example 1 was orally administered by force at a frequency of 3 times a week. After 1 week of the first administration, 20 mg of 3-MC(SIGMA) was dissolved in 2.0 ml of olive oil and 0.1 ml thereof (3-MC, 1 mg) was subcutaneously administered to the right side of flank. The same amount of olive oil was administered to the control group. Palpation was carried out once after 1 week of the subcutaneous administration, and a stiffness of 3 mm or more in diameter was regarded as a tumor. The palpation was carried out for 15 weeks. Additionally, 3 animals of each group were sacrificed 5 weeks after the administration and lymphocyte composition (NK cell) was measured.

The spleen of each of the sacrificed mice was extracted, and the spleen cells were suspended in 0.1% BSA-added PBS (BSA/PBS) and washing with centrifugal precipitation. After removing erythrocytes using a hypotonic solution (14 mmol/l $NH_4Cl$, 17 mmol/l Tris, pH 7.6), washing with BSA/PBS was carried out twice. The cell suspension was labeled by adding a fluorescence-labeled antibody of T cell [FITC-labeled anti-CD3 antibody, PE-labeled anti-CD19 antibody, PE-labeled anti-NK1.1 antibody, FITC-labeled anti-CD4 antibody or PE-labeled anti-CD8 antibody (Beckman Coulter, Hialeah, Fla.)]. The number of labeled lymphocytes was counted using a flow cytometry (FACSCalibur, Becton Dickinson).

Effect on 3-MC-Induced Fibrosarcoma Formation

Figure 3:
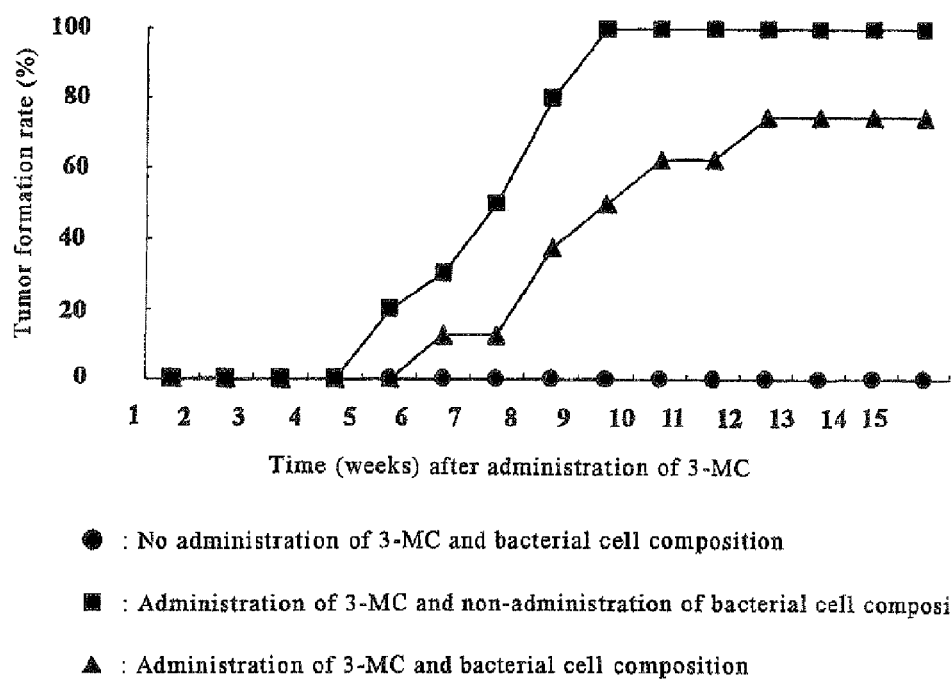
FIG. 3 is a drawing which shows effect of the administration of bacterial cell composition on 3-MC-induced fibrosarcoma formation.
Figure 4:
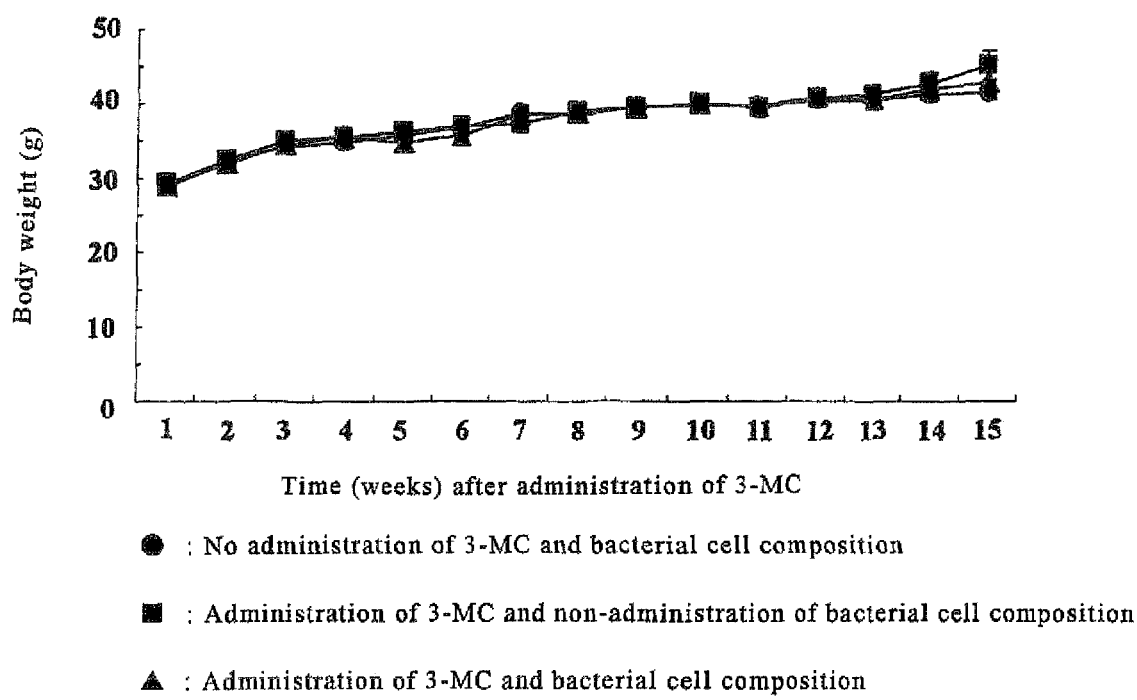
FIG. 4 is a drawing which shows influence of the administration of 3-MC and bacterial cell composition on weight gain.

As shown in FIG. 3, formation of tumor was not found in the mice to which olive oil was subcutaneously administered. In the test group in which 3-MC alone was administered, the tumor started to appear on the 5th week after the administration of 3-MC. The tumor forming ratio at this point of time was 20%. The forming ratio continued to increase thereafter, and the tumor was formed in all of the mice on the 9th week after the administration of 3-MC. On the other hand, the tumor forming ratio in the bacterial cell composition administration plot was 0% on the 5th week and 50% on the 9th week. Additionally, the forming ratio was 75% even after 15 weeks. Based on the result, it was confirmed that oral administration of the bacterial cell composition has the effect to delay or suppress 3-MC-induced tumor formation in mice. In this connection, the 3-MC treatment and the administration of the bacterial cell composition did not effect on the body weight gain of mice (FIG. 4).

Influence Upon Spleen Lymphocyte Composition

In order to confirm whether or not NK cell is concerned in delaying or suppressing effect of the tumor formation by the bacterial cell composition, lymphocyte composition in the spleen was measured. Since it was considered that a certain degree of period of time is necessary for showing effect of the bacterial cell composition, the measurement of lymphocyte was carried out just before the starting of tumor formation, namely 4 weeks after the administration of 3-MC. Significant differences were not found among the test groups, in terms of the body weight and weights of the liver and the spleen after 4 weeks and the ingested amount of feed (Table 17). However, ratios of the NK cell and NKT cell significantly increased by the administration of the bacterial cell composition (Table 18).

TABLE 17

Body weight and weights of the liver and spleen, and taking amount of feed

| 3-MC | Bacterial cell composition | Weight (g) | | | Feed Intake Amount (g/mouse/day) |
|---|---|---|---|---|---|
| | | The body | The liver | The spleen | |
| No administration | No administration | 35.1 ± 0.79 | 2.2 ± 0.1 | 0.101 ± 0.009 | 3.3 |
| Administration | No administration | 36.5 ± 0.67 | 2.2 ± 0.1 | 0.109 ± 0.036 | 3.1 |
| Administration | Administration | 35.4 ± 0.96 | 2.2 ± 0.1 | 0.098 ± 0.025 | 3.3 |

TABLE 18

Effect of the administration of 3-MC and bacterial cell composition on spleen lymphocyte composition

| 3-MC | Bacterial cell composition | Ratio of spleen lymphocytes (%) | | | | | |
|---|---|---|---|---|---|---|---|
| | | T cell | CD4 | CD8 | B cell | NK cell | NKT cell |
| No administration | No administration | 41.6 ± 5.1 | 33.0 ± 5.3 | 7.9 ± 0.5 | 51.0 ± 4.5 | 3.1 ± 0.8 | 0.03 ± 0.02 |
| Administration | No administration | 40.2 ± 5.8 | 25.7 ± 2.9 | 7.3 ± 0.6 | 51.5 ± 4.1 | 5.0 ± 0.4 | 0.33 ± 0.21 |
| Administration | Administration | 39.8 ± 5.3 | 26.9 ± 3.1 | 7.9 ± 1.3 | 50.9 ± 3.2 | 8.0 ± 0.7 | 0.66 ± 0.14 |

It is considered that NK cell has an important role in the initial stage of carcinogenesis. Additionally, it has been reported on a possibility that carcinogenesis is controlled by the increase of cytotoxic activity of NK cell. Additionally, as shown in Example 3, it was confirmed that the Th1/Th2 balance in the spleen inclines toward the Th1 side by the oral administration of the bacterial cell composition. Since it is known that a Th1 cytokine IFN-α accelerates growth of NK cell, it is considered that NK cell increases and delays or suppresses formation of cancer as a result.

Based on the above results, it was confirmed that a cancer in a region other than the large intestine can also be suppressed by oral administration of the bacterial cell composition.

While the present invention has been described in detail and with reference to specific embodiments thereof, it will be apparent to one skilled in the art that various changes and modifications can be made therein without departing from the spirit and scope of the invention.

This application is based on a Japanese patent application filed on Dec. 28, 2004 (Japanese Patent Application No. 2004-379693), and the entire contents thereof is herein incorporated by reference.

INDUSTRIAL APPLICABILITY

The present invention provides a bacterial cell composition having anticancer activity, immunostimulating effect, preventing and treating effect of inflammatory bowel disease, preventing effect of pathogen infection, preventing and treating effect of allergic disease and the like.

The invention claimed is:

1. An isolated *Butyrivibrio fibrisolvens* MDT-1 strain (FERM BP-10463) or a mutant strain thereof.

2. A bacterial cell composition comprising isolated bacterial cells of *Butyrivibrio fibrisolvens* MDT-1 (FERM BP-10463), or an isolated culture of *Butyrivibrio fibrisolvens* MDT-1 (FERM BP-10463), wherein the content of bacterial cells in the bacterial cell composition is about 0.01% of the total mass of the bacterial composition.

3. A pharmaceutical formulation, comprising the bacterial cell composition of claim 2 as an active ingredient and an ingestible carrier.

4. The pharmaceutical formulation of claim 3, wherein the ingestible carrier is a pharmaceutically acceptable carrier.

5. The pharmaceutical formulation of claim 4, wherein the pharmaceutically acceptable carrier is in the form of a capsule, a tablet, or a powder.

6. The pharmaceutical formulation of claim 3, wherein the ingestible carrier is a food product.

* * * * *